United States Patent
Parker et al.

(10) Patent No.: US 7,083,413 B2
(45) Date of Patent: Aug. 1, 2006

(54) METHOD FOR PRODUCING DENTAL MODELS

(76) Inventors: Kammy Parker, 1411 J N. Valley Mills #318, Waco, TX (US) 76710; Doris Craig, 310 Jampico, Hewitt, TX (US) 76643; Jerry Gaubert, 5322 Goodwin Ave., Dallas, TX (US) 75206; James Bereck, 213 Oak Creek Cir., McGregor, TX (US) 76657

( * ) Notice: Subject to any disclaimer, the term of this patent is extended or adjusted under 35 U.S.C. 154(b) by 147 days.

(21) Appl. No.: 10/653,702

(22) Filed: Sep. 2, 2003

(65) Prior Publication Data

US 2005/0048442 A1    Mar. 3, 2005

(51) Int. Cl.
    *A61C 11/00* (2006.01)

(52) U.S. Cl. .......................... 433/213; 433/34; 433/214

(58) Field of Classification Search .................. 433/34, 433/37, 45, 47, 213, 214; 29/896.1
    See application file for complete search history.

(56) References Cited

U.S. PATENT DOCUMENTS

| | | | | | |
|---|---|---|---|---|---|
| 20,754 | A | * | 6/1858 | Wright | 433/213 |
| 752,378 | A | * | 2/1904 | Dailey | 433/37 |
| 4,386,964 | A | * | 6/1983 | Herbert | 106/132.2 |
| 4,721,464 | A | * | 1/1988 | Roden et al. | 433/74 |
| 4,726,768 | A | * | 2/1988 | Lee | 433/34 |
| 4,865,546 | A | * | 9/1989 | Naylor | 433/213 |
| 5,538,551 | A | * | 7/1996 | Desbiens | 106/128.1 |
| 5,647,744 | A | * | 7/1997 | Squicciarini | 433/34 |
| 5,911,580 | A | * | 6/1999 | Sharp et al. | 433/213 |
| 5,980,880 | A | * | 11/1999 | Love | 424/76.1 |
| 6,786,722 | B1 | * | 9/2004 | Craig et al. | 433/48 |

* cited by examiner

*Primary Examiner*—Ralph A. Lewis
(74) *Attorney, Agent, or Firm*—David Henry

(57) ABSTRACT

An improved method for producing dental models through use of a dough-like modeling filler material as a base, embedding a dental preliminary impression in such based, using a spring-form mold ring embedding in the base to surround the preliminary impression, and pouring dental casting material within the bounds of the mold ring to form a positive dental model.

2 Claims, 5 Drawing Sheets

METHOD FOR PRODUCING DENTAL MODELS

BACKGROUND OF THE INVENTION

1. Field of the Invention

The present invention relates to dental modeling.

2. Background Information

Whatever the time consumed in producing a dental model for dentures or other dental or orthodontic work, any savings of time is a highly desirable objective. As with any service or manufacturing activity, time is indeed money in the dental, orthodontic and dental laboratory fields.

Ordinarily, the process for setting up a dental model consumes approximately a half hour. Wax or other filler material is built up around the primary impression and carefully hand-worked to prevent any voids, as well as to produce a "feathered" edge at the impression line. Only after this hand-crafted based for the primary impression is created and find-tuned, can the casting material be poured over the impression for the positive dental model. This process is repeated thousands of times each day around the world.

It would be beneficial to a very significant degree to provide some apparatus, material and/or method by which the time consumed in setting up a dental model could be reduced, even if to a minimal degree. It would be further beneficial if the method were to be in the nature of a much simplified version of the conventional process, whereby the level of skill required to carry out the process would be substantially lower, thereby potentially reducing the propensity for errors.

SUMMARY OF THE INVENTION

In view of the foregoing, it is an object of the present invention to provide an improved method for producing dental models.

It is another object of the present invention to provide an improved method for producing dental models which affords time savings when compared to conventional methods.

It is another object of the present invention to provide an improved method for producing dental models which requires a lesser skill level when compared to that required in practicing conventional methods.

It is another object of the present invention to provide an improved method for producing dental models which obviates time consuming steps in producing such models.

In satisfaction of these and related objects, the present method provides a new and useful method for producing dental models. The present method reducing set-up time from approximately one-half hour to approximately five minutes.

The present method, while quite simple, will revolutionize the dental lab field with respect to the methods used to produce dental models, and dramatically reduce time (and associated costs) consumed in doing so.

The present method involves the use of a proprietary void filler material (the subject of co-pending patent applications) as a base upon which a preliminary impression is embedded. A breakaway cookie cutter-like mold ring is used to confine casting material during curing, after which the filler material easily pulls away from the positive model to produce a finished product.

DETAILED DESCRIPTION OF THE PREFERRED EMBODIMENT

A. FILLER MATERIAL

Figure 1:
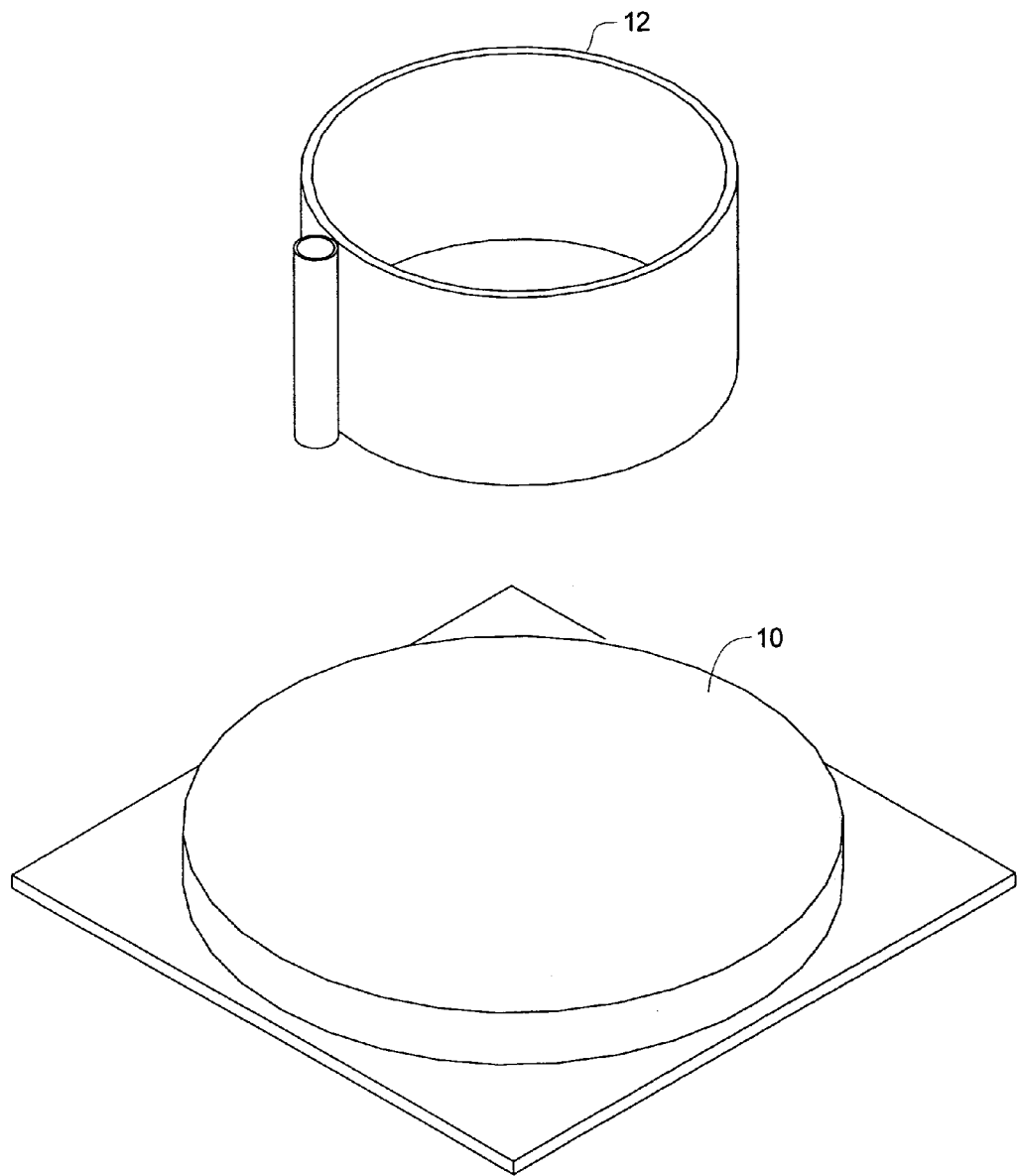
FIG. 1 is a perspective view of the spring-form mold ring and a user-formed base of filler material.

The present method, while perhaps performable using an alternative filler material, is believed best performed through use of a proprietary dental filler material sold by Dental Creations, Ltd. of Waco, Tex. under the WONDER FILL trademark (the subject of pending patent applications assigned to Dental Creations, Ltd.), the unique characteristics of which afford superior conformity with the irregularities of dental impressions, yet readily release therefrom and from all apparatus and accessories after casting.

The filler material is of a formulation developed after extensive testing, re-formulation and refinement by Dental Creations, Ltd. researchers, and is prepared according to the hereafter described method.

While commercial production will require proportional scale up, but a single, 51 oz. batch "recipe" for the present filler is as follows:

3 cups standard baking flour

1½ cups salt 3 cups water 6 tbsp. cream of tartar 6 tbsp. vegetable cooking oil 15 drops peppermint oil 6 drops food color (optional)

According to conventional conversions, the above measurements can be converted as follows: 2 tablespoons=1 part by volume and 1 cup=8 parts by volume, with the measurements being given in drops being appropriately scaled-up based on the most basic of batch manufacturing experience.

The precise method of manufacture of the present filler material is, as mentioned before, the result of much experimentation and adjustment. The process, in its presently believed best mode (for making one 51 oz. batch, but scalable for larger batches) is as follows:

Mixing

1. Measure vegetable oil and water.

2. Add the food coloring to warm tap water (approximately 90°–100° F. [not substantially hotter or cooler], and stir thoroughly.

3. Pour the water and food coloring mixture into a mixing bowl appropriate to the size of the intended filler batch.

4. Add dry ingredients slowly and then stir completely.

5. Then add the vegetable oil.

6. Place the mixing bowl onto a commercial mixer stand (HOBART model A200 is exemplary for this method), attach its spiral whisk to the mixer, and latch mixing bowl on both sides.

7. Set timer for 30 seconds and mix ingredients on mixer's lowest speed.

8. Turn the mixer up to a higher, medium speed and mix for an additional minute.

9. Reset timer for 1 minute and mix on mixer's highest (3rd speed on a three or more speed mixer).

10. Stop the mixer and timer.

11. After the mixture is poured, scrape the excess from sides into the bottom of mixing bowl.

Total mixing time: 2 minutes and 30 seconds.

Cooking

1. Set a commercial, flat-topped grill to 275° F. (assuring that grill is clean and does not have dried dough on it from prior batches).

2. Starting from the back of the grill pour mixture onto the grill from left to right and leave for 2 minutes and 45 seconds.

3. Turn product onto the other side and cut into 2 rows of squares the size of the spatula beginning on the row nearest person cooking. This should take approximately 1 minute to 1 minute and 15 seconds.

4. Then leave on the grill for 45 seconds.

5. Work into a ball for 45 seconds.

6. Then knead on grill for 1 minute and 15 seconds.

Kneading

1. Place a kneading bowl onto a kneading stand (HOBART model D330 is exemplary for the present method), attach the flat paddle style beater to the kneading machine, and latch kneading bowl on both sides.

2. Add aromatic (peppermint) oil to dough.

3. Set kneader to high (#3) speed and knead for 45 seconds.

4. Spread mixture out on packaging table for cooling, and allow to cool for 25 minutes.

The kneading bowl must be cleaned after the sixth use and sprayed with vegetable cooking spray.

Packaging

Do Not Package Product Hot!!

1. Using the scale, weigh the product to 3 lbs. 4 oz.

2. Hand knead the product, form in a smooth ball, and lightly spray with vegetable oil cooking spray (such as PAM brand cooking spray) and spread around the formed ball.

3. Let product set for 30 seconds.

4. Place product in plastic bag and press down to remove air.

5. Close the bag.

It should be understood that variations in constituents, such as moisture in flour, ambient temperature in the manufacturing facility, water quality, etc. may require slight variations in cooking, kneading, and cooling times, as well as slight adjustments in relative volumes of constituents. However, such variations will be within the skills of any competent batch manufacturing supervisor or manager. Therefore, quantities and cooking, kneading and cooling times, while found to be optimal in working conditions of relatively normal range of temperature and humidity, and using constituents of standard quality (14% moisture in standard baking flour, for example), should, in other conditions or circumstances, be understood to be approximate. If adjusting cooking times for a minute one way or the other, or, for example, varying constituent amounts by a relative or so, should be required to meet other than standard conditions or circumstances to produce product of desirable characteristics, such should be understood to still fall within the scope of the present invention.

It should also be noted that the use of peppermint oil (or an equivalent aromatic oil, if such can be determined to truly be equivalent for present purposes) is not merely for aesthetic purposes. Experiments using and omitting the peppermint oil have revealed, contrary to earlier assumptions, that such is a vital component to the present filler material. When the peppermint oil is omitted, the filler exhibits noticeably inferior characteristics and shelf life performance. It is believed that the oil (particularly when added in the sequence discussed above) has some marked effect on moisture retention, thereby preserving optimal texture, and preventing "crystallization." It is suspected that wintergreen, spearmint, or even clove oils may perform equivalent functions to that of peppermint oil in this context, but such has not yet been determined at this time of this filing.

B. MODELING METHOD

Referring to FIG. 1—after a preliminary impression is made in the conventional manner, a practitioner of the present method forms a user-formed base 10 of filler material, somewhat resembling a hamburger patty in size and shape.

Figure 2:
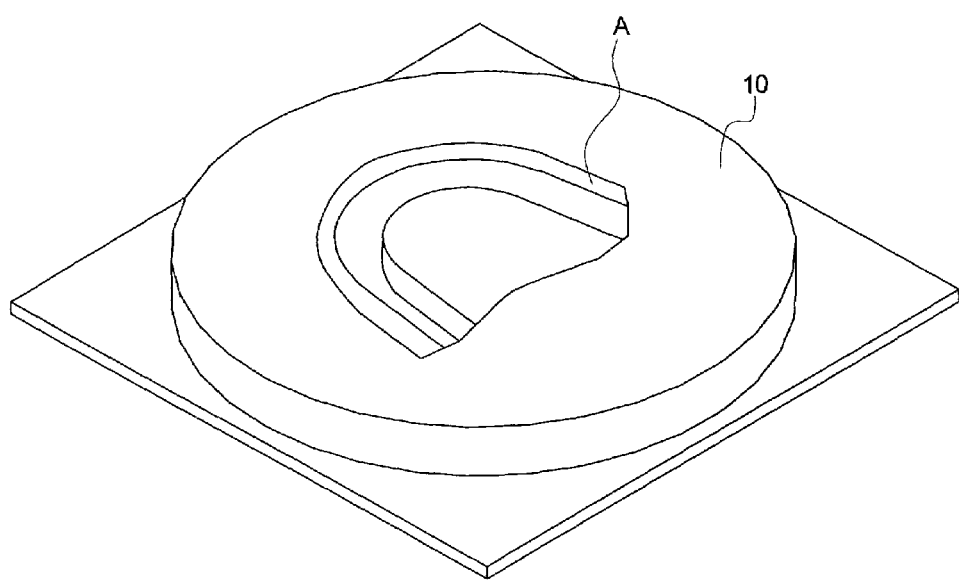
FIG. 2 is a perspective view of a preliminary impress embedded in the user-formed based of FIG. 1.
Figure 3:
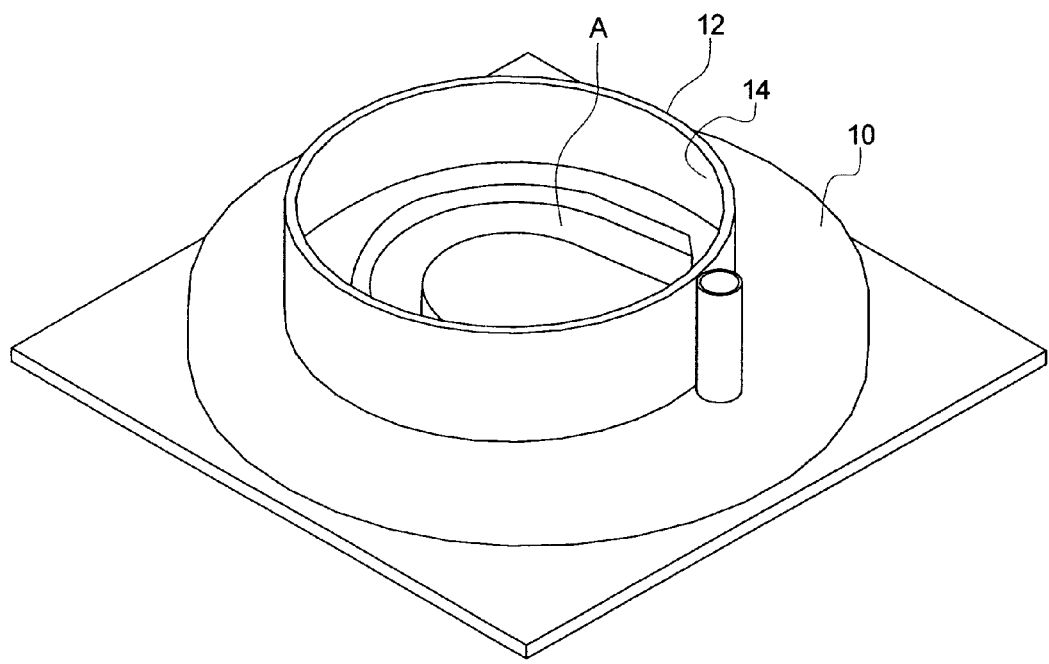
FIG. 3 is a perspective view of the spring-form mold ring and user-formed based of FIG. 1 and preliminary impression of FIG. 2, with the spring-form mold ring pressed into place onto user-formed base to form a mold.

Referring to FIGS. 1 and 2—a user next embeds a preliminary impression A substantially centrally of the user formed base 10, ensuring that the filler closely envelopes the preliminary impression A, without any perceptible voids between the two. After conforming the filler of user-formed base 10 to the preliminary impression A, spring-form mold ring 12 is pressed into the user-formed based 10 to surround the preliminary impression A and form a mold chamber 14.

Figure 4:
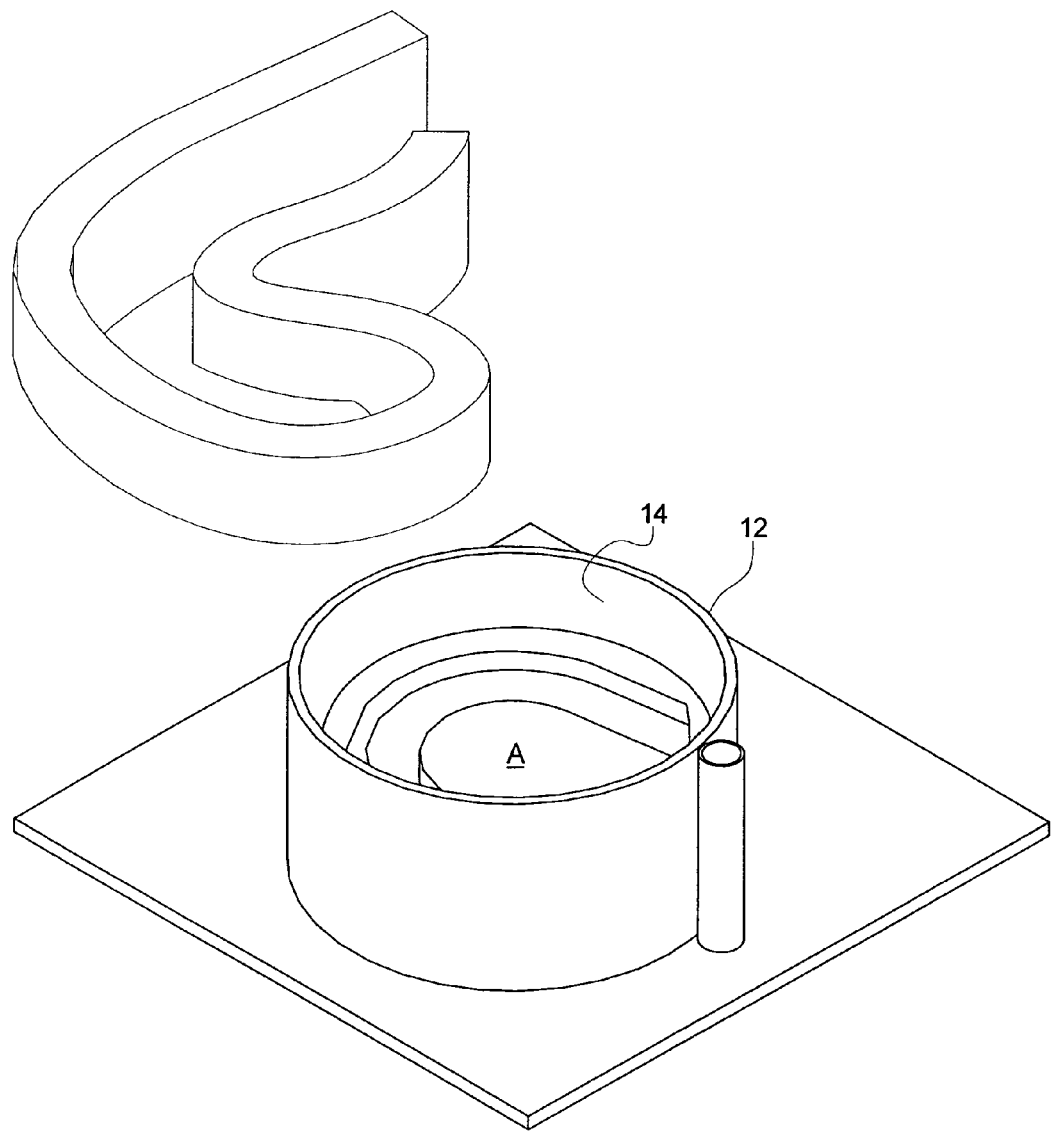
FIG. 4 is a perspective view of the assemblage of FIG. 3 with excess material outside of spring-form mold ring removed.

As shown in FIG. 4, excess filler material, outside of spring form mold ring 12 is removed for convenience of handling, after which conventional casting material (not shown in the drawings) is poured into mold chamber 14 and, according to conventional practice, is placed on a vibrator for removing entrained air bubbles.

Figure 5:
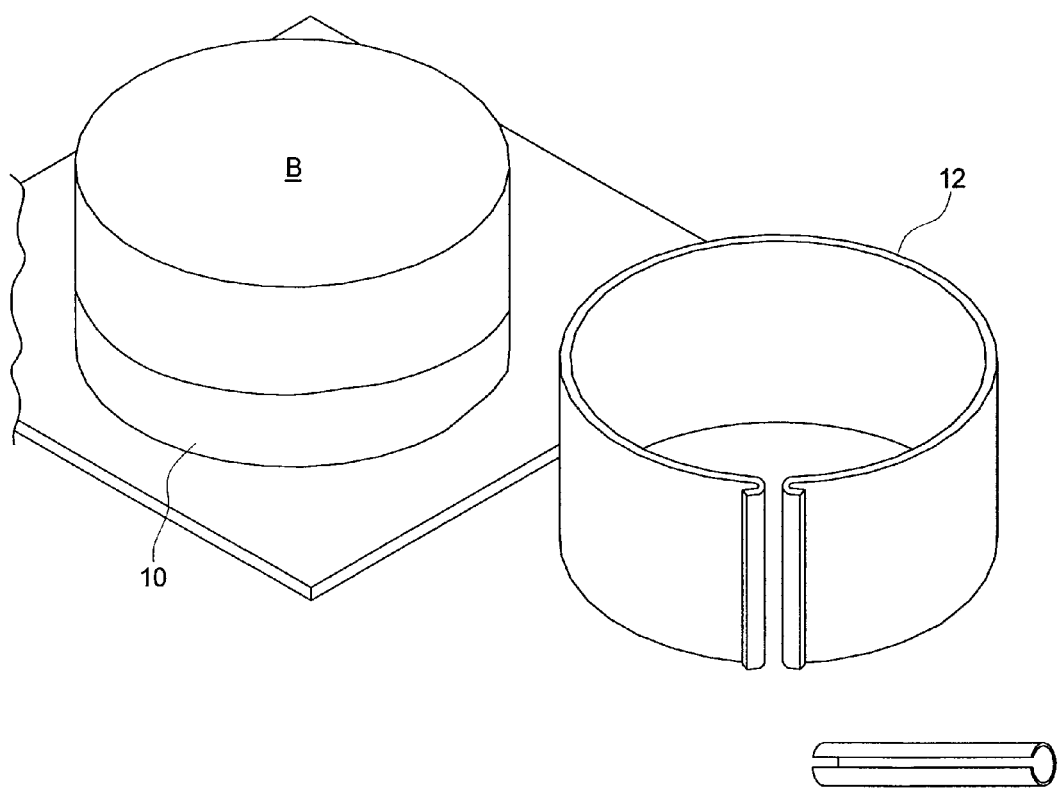
FIG. 5 is a perspective view of spring form mold ring of FIG. 1 removed from the remainder of the assemblage of FIG. 3 after casting material was added into the mold assemblage and allowed to cure.

As shown in FIG. 5, after a suitable curing time, spring form mold ring 12 is removed from the now-cured positive model B, and the associated preliminary impression A and filler material of user-formed base 12, the latter two components are removed from the positive model B, and the process is complete.

Tests have revealed that the above process saves approximately 85% in processing time, otherwise consumed by producing a dental model by conventional methods.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:
1. An improved method for producing a dental model comprising the steps of:
   forming a user-formed base of moldable, dough-like material;
   embedding a dental preliminary impression in a surface thereof;
   embedding a mold ring member into said surface of said user-formed based in a position to encircle said preliminary impression within the bounds of said mold ring member;
   inserting dental model casting material atop said user-formed base and said preliminary dental impression;
   after curing of said casting material, removing said mold ring member from the combined casting material, preliminary impression and user-formed base; and
   removing said user-formed base and preliminary impression from the cured said dental casing material.

2. The method of claim 1 wherein said dough-like material comprises constituents of approximately the ratios of:
   24 parts flour by volume;
   12 parts salt by volume;
   24 parts water by volume;
   1 part cream of tartar; and
   1 part cooking oil.

* * * * *